(12) United States Patent
Tateno et al.

(10) Patent No.: US 12,308,105 B2
(45) Date of Patent: May 20, 2025

(54) APPARATUS, METHOD, AND PROGRAM FOR ASSISTING CREATION OF CONTENTS TO BE USED IN INTERVENTIONS, AND COMPUTER-READABLE RECORDING MEDIUM

(71) Applicant: SMN CORPORATION, Tokyo (JP)

(72) Inventors: Kei Tateno, Tokyo (JP); Hayato Sakata, Tokyo (JP); Noriyuki Yamamoto, Tokyo (JP)

(73) Assignee: SMN CORPORATION, Tokyo (JP)

( * ) Notice: Subject to any disclaimer, the term of this patent is extended or adjusted under 35 U.S.C. 154(b) by 442 days.

(21) Appl. No.: 17/975,937

(22) Filed: Oct. 28, 2022

(65) Prior Publication Data

US 2023/0050451 A1 Feb. 16, 2023

Related U.S. Application Data

(63) Continuation of application No. PCT/JP2021/016812, filed on Apr. 27, 2021.

(30) Foreign Application Priority Data

May 22, 2020 (JP) .................................. 2020-089377

(51) Int. Cl.
*G16H 20/70* (2018.01)
*G16H 50/20* (2018.01)

(52) U.S. Cl.
CPC ............. *G16H 20/70* (2018.01); *G16H 50/20* (2018.01)

(58) Field of Classification Search
CPC ................................ G16H 20/70; G16H 50/20
See application file for complete search history.

(56) References Cited

U.S. PATENT DOCUMENTS

| | | | | |
|---|---|---|---|---|
| 8,762,193 | B2 * | 6/2014 | Maga | G06Q 30/02 705/7.29 |
| 10,068,188 | B2 * | 9/2018 | Chittilappilly | G06Q 30/0246 |
| 11,182,822 | B2 * | 11/2021 | Shani | G06Q 30/0275 |
| 2013/0226710 | A1 | 8/2013 | Plut | |

FOREIGN PATENT DOCUMENTS

| | | |
|---|---|---|
| JP | 2015-53071 A | 3/2015 |
| JP | 2016-177536 A | 10/2016 |
| JP | 2017-168078 A | 9/2017 |

OTHER PUBLICATIONS

International Search Report and Written Opinion issued on Jul. 27, 2021 in corresponding application No. PCT/JP2021/016812; 11 pgs.

* cited by examiner

*Primary Examiner* — Michael I Ezewoko
(74) *Attorney, Agent, or Firm* — Maier & Maier, PLLC

(57) ABSTRACT

A processing unit includes a contribution-degree calculation unit configured to calculate contribution degrees that indicate respective degrees by which a plurality of attribute items included as predetermined attributes of one target contribute to a predicted intervention effect, the calculating being performed on a basis of an estimation model for estimating the predicted intervention effect from the predetermined attributes of the one target. The predicted intervention effect on the one target is a numerical value corresponding to an increase in gain to a beneficiary, the gain being expected to be larger in a case where an intervention is implemented to the one target than in a case where the intervention is unimplemented to the one target.

9 Claims, 11 Drawing Sheets

FIG.3A

| TARGET ID | SEX | AGE | REGION | OCCUPATION | NUMBER OF TIMES OF VISITS TO SITE | --- |
|---|---|---|---|---|---|---|
| 1001 | FEMALE | 20s | TOKYO | COMPANY EMPLOYEE | 12 | |
| 1002 | FEMALE | 40s | KANAGAWA | COMPANY EMPLOYEE | 3 | |
| 1003 | MALE | 20s | NAGOYA | PUBLIC EMPLOYEE | 4 | |
| 1004 | FEMALE | 30s | TOKYO | UNEMPLOYED | 10 | |
| 1005 | MALE | 50s | OSAKA | SELF-EMPLOYED | 4 | |
| 1006 | MALE | TEEN | FUKUOKA | STUDENT | 9 | |
| --- | --- | --- | --- | --- | --- | |

FIG.3B

| INTERVENTION ID | CATEGORY OF COMMERCIAL PRODUCT | CONTENT ID | NUMBER OF TIMES OF INTERVENTIONS | --- |
|---|---|---|---|---|
| T001 | A | C001 | 1 | |
| T002 | B | C002 | 1 | |
| T003 | C | C003 | 1 | |
| T004 | D | C004 | 3 | |
| T005 | E | C005 | 2 | |
| --- | --- | --- | --- | |

FIG.3C

| CONTENT ID | NUMBER OF CHARACTERS | HUMAN | ANIMAL | BACKGROUND COLOR | --- |
|---|---|---|---|---|---|
| C001 | 15 | DEPICTED | NOT DEPICTED | WHITE | |
| C002 | 200 | NOT DEPICTED | NOT DEPICTED | BLUE | |
| C003 | 30 | NOT DEPICTED | DEPICTED | YELLOW | |
| C004 | 50 | NOT DEPICTED | NOT DEPICTED | WHITE | |
| C005 | 110 | DEPICTED | NOT DEPICTED | PURPLE | |
| --- | --- | --- | --- | --- | |

| TARGET ID | INTERVENTION | RESULT (PURCHASE) |
|---|---|---|
| 1001 | NOT IMPLEMENTED | PURCHASED |
| 1002 | T001 | PURCHASED |
| 1003 | T001 | NOT PURCHASED |
| 1004 | T001 | PURCHASED |
| 1005 | NOT IMPLEMENTED | NOT PURCHASED |
| 1006 | NOT IMPLEMENTED | NOT PURCHASED |
| --- | --- | --- |

INTERVENTION IMPLEMENTED

| TARGET ID | RESULT (PURCHASE) |
|---|---|
| 1002 | PURCHASED |
| 1003 | NOT PURCHASED |
| 1004 | PURCHASED |
| --- | --- |

INTERVENTION NOT IMPLEMENTED

| TARGET ID | RESULT (PURCHASE) |
|---|---|
| 1001 | PURCHASED |
| 1005 | NOT PURCHASED |
| 1006 | NOT PURCHASED |
| --- | --- |

FIG.5

| TARGET ID | SEX | AGE | NUMBER OF TIMES OF VISITS TO SITE |
|---|---|---|---|
| 1001 | FEMALE | 20s | 12 |
| 1002 | FEMALE | 40s | 3 |
| 1003 | MALE | 20s | 4 |
| 1004 | FEMALE | 30s | 10 |
| 1005 | MALE | 50s | 4 |
| 1006 | MALE | TEEN | 9 |
| --- | --- | --- | --- |

FIG.6A

| TARGET ID | SEX | AGE | NUMBER OF TIMES OF VISITS TO SITE (311) | RESULT (PURCHASE) (341) |
|---|---|---|---|---|
| 1002 | FEMALE | 40s | 3 | PURCHASED |
| 1003 | MALE | 20s | 4 | NOT PURCHASED |
| 1004 | FEMALE | 30s | 10 | PURCHASED |
| ---- | ---- | ---- | ---- | ---- |

INTERVENTION IMPLEMENTED $\Rightarrow Y = \mu_1(X)$

FIG.6B

| TARGET ID | SEX | AGE | NUMBER OF TIMES OF VISITS TO SITE (311) | RESULT (PURCHASE) (341) |
|---|---|---|---|---|
| 1001 | FEMALE | 20s | 12 | PURCHASED |
| 1005 | MALE | 50s | 4 | NOT PURCHASED |
| 1006 | MALE | TEEN | 9 | NOT PURCHASED |
| ---- | ---- | ---- | ---- | ---- |

INTERVENTION NOT IMPLEMENTED $\Rightarrow Y = \mu_0(X)$

FIG.7

| TARGET ID | PREDICTED INTERVENTION EFFECT |
|---|---|
| 2001 | 0.143 |
| 2002 | 0.631 |
| 2003 | 0.226 |
| 2004 | 0.053 |
| 2005 | 0.376 |
| 2006 | 0.112 |
| --- | --- |

FIG.8

| ATTRIBUTE ITEM | WEIGHTING COEFFICIENT |
|---|---|
| SEX - MALE | +2.4 |
| SEX - FEMALE | -1.3 |
| AGE - 20s | +0.1 |
| AGE - 30s | +3.4 |
| AGE - 40s | +2.1 |
| AGE - 50s | -0.8 |
| NUMBER OF TIMES OF VISITS TO SITE | +1.4 |
| --- | --- |

APPARATUS, METHOD, AND PROGRAM FOR ASSISTING CREATION OF CONTENTS TO BE USED IN INTERVENTIONS, AND COMPUTER-READABLE RECORDING MEDIUM

This application is a Continuation Application of PCT International Application No. PCT/JP2021/016812, filed on Apr. 27, 2021, and the PCT International Application is based upon and claims the benefit of priority from Japanese Patent Application No. 2020-089377, filed on May 22, 2020, the entire contents of which are incorporated herein by reference.

TECHNICAL FIELD

The present invention relates to an apparatus, a method, and a program that assist creation of contents to be used in interventions, and relates to a computer-readable recording medium that records the program.

BACKGROUND

A technology for individually predicting effects of interventions (such as advertisements and medical practice) to intervention targets (such as users of the WEB to whom the advertisements are individually displayed and patients to whom the medical treatment such as surgery is individually applied) has been known. For example, Japanese Patent Application Laid-open No. 2015-53071 discloses an invention that allows measured causal effects to be utilized in information transmission.

SUMMARY

Incidentally, in the field of WEB advertising, contents such as banners to be presented to the users may have significant influence on purchase rates of commercial products. Thus, it is important to create contents that can increase the purchase rates. However, hitherto, the contents have been created without clear guidelines on which factor of the contents has influence on the purchase rates. Thus, a proportion in which the creation depends on senses of creators of the contents has been high, and hence there has been a disadvantage that creation of contents having great advertising effects is difficult.

The present invention has been made in view of such circumstances, and it is an object thereof to provide an apparatus, a method, and a program that are capable of facilitating creation of contents having greater intervention effects, and to provide a computer-readable recording medium that records the program.

According to a first aspect of the present invention, there is provided an apparatus configured to assist creation of contents to be used in interventions, the apparatus including:
a processing unit including at least one processor; and
a storage unit configured to store a command to be executed by the processing unit,
in which the interventions include presentation of the contents to a plurality of targets so that the plurality of targets provoke reactions that a beneficiary wants,
in which, among respective predicted-intervention effects on the plurality of targets, one predicted-intervention effect on one target among the plurality of targets is a numerical value corresponding to an increase in gain to the beneficiary, the gain being expected to be larger in a case where a corresponding one intervention among the interventions is implemented to the one target than in a case where the corresponding one intervention is unimplemented to the one target,
in which the gain is a numerical value that is set in accordance with a result of a corresponding one reaction by the one target among the reactions,
in which the processing unit executes, in accordance with the command,
a process of calculating contribution degrees that indicate respective degrees by which a plurality of attribute items included as predetermined attributes of the one target contribute to the one predicted-intervention effect, the calculating being performed on a basis of an estimation model for estimating the one predicted-intervention effect from the predetermined attributes of the one target,
a process of generating a display screen that can be displayed on a display to be used in work of creating the contents, and
in which the process of generating the display screen includes generating the display screen on which at least one contribution degree among the contribution degrees calculated respectively with regard to the plurality of attribute items is displayed.

According to a second aspect of the present invention, there is provided a method of assisting creation of contents to be used in interventions,
the interventions including presentation of the contents to a plurality of targets so that the plurality of targets provoke reactions that a beneficiary wants,
among respective predicted-intervention effects on the plurality of targets, one predicted-intervention effect on one target among the plurality of targets being a numerical value corresponding to an increase in gain to the beneficiary, the gain being expected to be larger in a case where a corresponding one intervention among the interventions is implemented to the one target than in a case where the corresponding one intervention is unimplemented to the one target,
the gain being a numerical value that is set in accordance with a result of a corresponding one reaction by the one target among the reactions,
the method including:
calculating, by at least one computer, contribution degrees that indicate respective degrees by which a plurality of attribute items included as predetermined attributes of the one target contribute to the one predicted-intervention effect, the calculating being performed on a basis of an estimation model for estimating the one predicted-intervention effect from the predetermined attributes of the one target; and
generating, by the at least one computer, a display screen that can be displayed on a display to be used in work of creating the contents,
in which the generating of the display screen by the at least one computer includes generating the display screen on which at least one contribution degree among the contribution degrees calculated respectively with regard to the plurality of attribute items is displayed.

According to a third aspect of the present invention, there is provided a program which assists creation of contents to be used in interventions,
the interventions including presentation of the contents to a plurality of targets so that the plurality of targets provoke reactions that a beneficiary wants,
among respective predicted-intervention effects on the plurality of targets, one predicted-intervention effect on one target among the plurality of targets being a numerical value corresponding to an increase in gain to the beneficiary, the gain being expected to be larger in a case where a corresponding one intervention among the interventions is implemented to the one target than in a case where the corresponding one intervention is unimplemented to the one target, the gain being a numerical value that is set in accordance with a result of a corresponding one reaction by the one target among the reactions, the program causing at least one computer to execute:
a process of calculating contribution degrees that indicate respective degrees by which a plurality of attribute items included as predetermined attributes of the one target contribute to the one predicted-intervention effect, the calculating being performed on a basis of an estimation model for estimating the one predicted-intervention effect from the predetermined attributes of the one target; and
a process of generating a display screen that can be displayed on a display to be used in work of creating the contents,
in which the process of generating the display screen includes generating the display screen on which at least one contribution degree among the contribution degrees calculated respectively with regard to the plurality of attribute items is displayed.

According to a fourth aspect of the present invention, there is provided a computer-readable recording medium that records the program according to the third aspect.

According to the present invention, it is possible to provide an apparatus, a method, and a program that are capable of facilitating creation of contents having greater intervention effects, and to provide a computer-readable recording medium that records the program.

BRIEF DESCRIPTION OF DRAWINGS

FIG. 3A is a table showing an example of target information, FIG. 3B is a table showing an example of intervention information, and FIG. 3C is a table showing an example of content information.

FIG. 4A is a table showing an example of result information, FIG. 4B is a table showing an example of intervened-group result information, and FIG. 4C is a table showing an example of non-intervened-group result information.

FIG. 5 is a table showing an example of target attribute information.

FIG. 6A is a table showing the intervened-group result information and the target attribute information to be used in generating a first-gain estimation model, and FIG. 6B is a table showing the non-intervened-group result information and the target attribute information to be used in generating a second-gain estimation model.

FIG. 7 is a table showing an example of predicted intervention effects calculated respectively with regard to targets.

FIG. 8 is a table showing an example of respective weighting coefficients of attribute items in a linear estimation model.

DETAILED DESCRIPTION OF THE EMBODIMENTS

Figure 1:
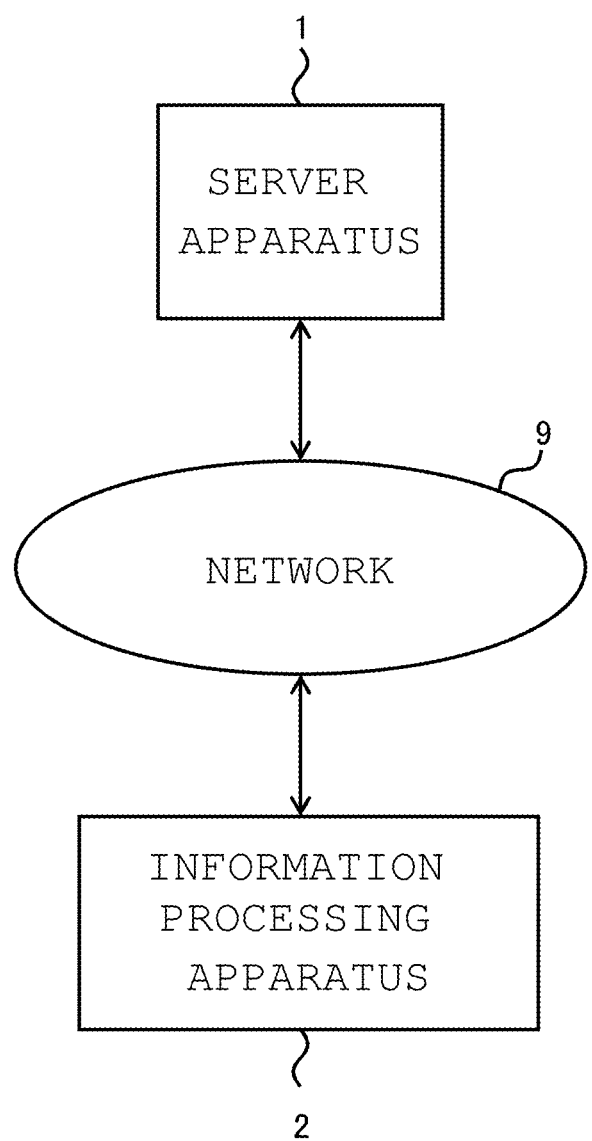
FIG. 1 is a diagram showing an example of a configuration of a system including a server apparatus according to an embodiment of the present invention.

FIG. 1 is a diagram showing an example of a configuration of a system including a server apparatus 1 according to an embodiment of the present invention. The system shown in FIG. 1 includes the server apparatus 1 and an information processing apparatus 2 that are communicable with each other via a network 9 such as the Internet. The server apparatus 1 is an apparatus to be managed by an entity that implements interventions (below, sometimes referred to as an "intervener"). The information processing apparatus 2 is a terminal apparatus to be used in work of creating contents for the interventions (such as banners for advertising). Herein, the "intervention" means an action to be taken for targets so that the targets provoke predetermined reactions that a beneficiary wants. In addition, the "beneficiary" means an entity that receives a resultant profit from the intervention. In the following description, as an example, the "intervention" is defined as advertising on a WEB site, the "target" is defined as a user on the Internet who visits the WEB site, the "beneficiary" is defined as an advertiser who requests the advertising on the WEB site, and the "intervener" is defined as a service provider involved in a service of the advertising on the WEB site in response to the request from the advertiser. Note that, the advertising on the WEB site is merely an example of the "intervention," and the present invention is not limited to this example. In other words, concepts of the "intervention," the "intervener," the "beneficiary," and the like of the present invention are applicable also to various other fields.

Figure 2:
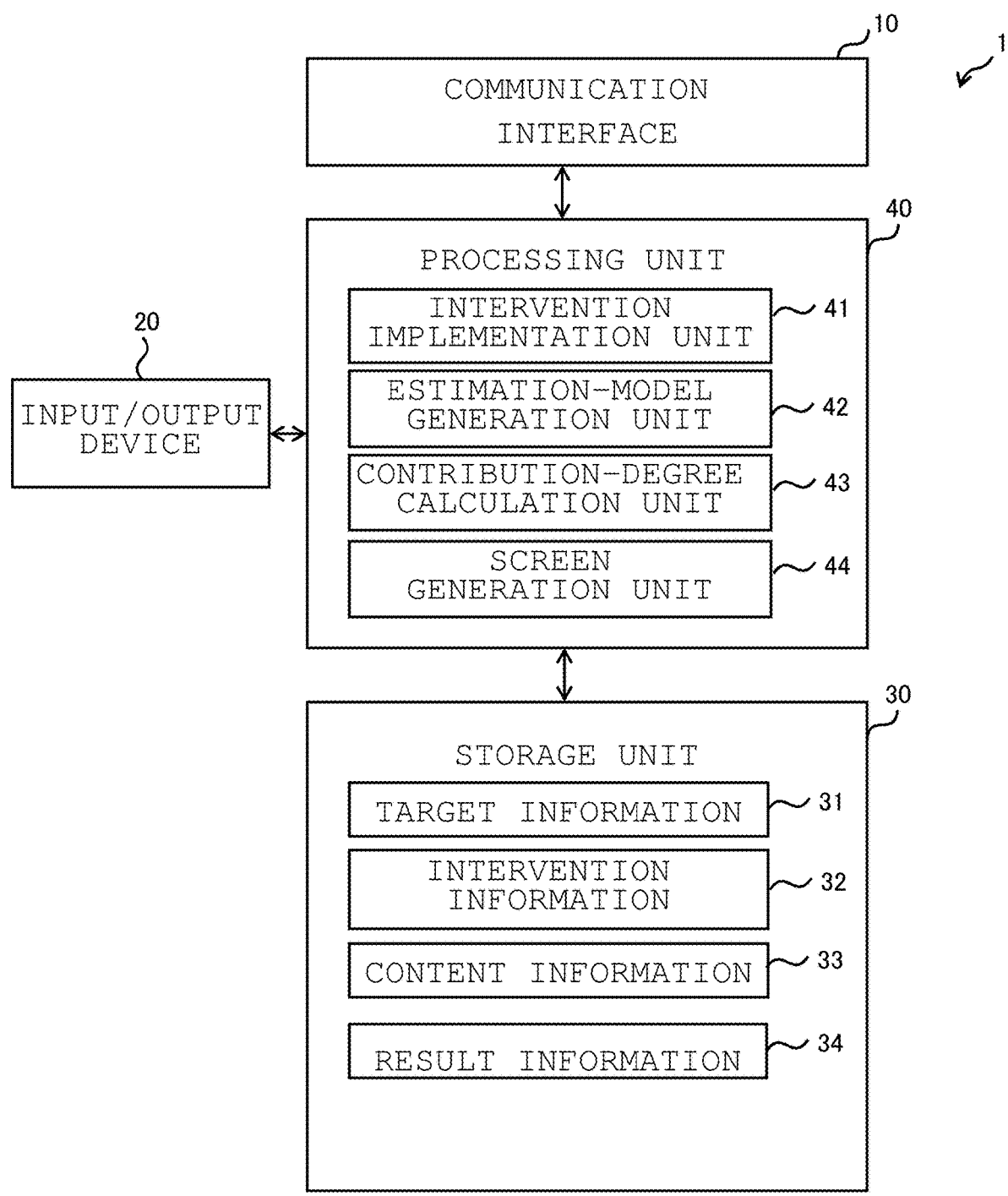
FIG. 2 is a diagram showing an example of a configuration of the server apparatus according to the embodiment of the present invention.

FIG. 2 is a diagram showing an example of a configuration of the server apparatus 1 according to this embodiment. The server apparatus 1 shown in FIG. 1 includes a communication interface 10, an input/output device 20, a storage unit 30, and a processing unit 40.

The communication interface 10 is an apparatus for communicating with other apparatuses (such as the information processing apparatus 2) via the network 9, and includes a communication device such as a network interface card that performs the communication according to a predetermined communication standard such as Ethernet (trademark) or a wireless LAN.

The input/output device 20 has at least one of an input function to input instructions in response to operations by a user and other information to the processing unit 40, and an output function to output information from the processing unit 40. For example, the input/output device 20 includes at least one of a device having the input function, such as a keyboard, a mouse, a touchpad, a microphone, or a camera, a device having the output function, such as a display or a speaker, and a device having an input/output function, such as a touchscreen.

The storage unit 30 stores a program including a command to be executed by the processing unit 40, and stores, for example, data to be temporarily stored during processes to be executed by the processing unit 40, data to be used in the processes to be executed by the processing unit 40, and resultant data from the processes executed by the processing unit 40. More specifically, the storage unit 30 stores, for example, target information 31 (FIG. 3A), intervention information 32 (FIG. 3B), and content information 33 (FIG. 3C) described below.

The program to be stored in the storage unit 30 may be, for example, read out of a storage apparatus (such as a USB memory) connected to an interface such as an USB of the input/output device 20, may be read out of a computer-readable recording medium (a non-transitory tangible recording medium such as an optical disk) with a recording-medium reading apparatus of the input/output device 20, or may be downloaded via the communication interface 10 from another apparatus connected to the network 9.

The storage unit 30 includes main storage apparatuses (such as a ROM and a RAM), and auxiliary storage apparatuses (such as a flash memory, an SSD, a hard disk, and an optical disk). The storage unit 30 may be constituted by one among the plurality of these storage apparatuses, or may be constituted by the plurality of these storage apparatuses. These storage apparatuses constituting the storage unit 30 are connected to the processing unit 40 via a bus of a computer or other communication means.

The processing unit 40 collectively controls overall operations in the server apparatus 1, and executes predetermined information processes. The processing unit 40 includes one or more processors (such as a CPU or an MPU) that execute, for example, processes in accordance with the commands of the one or more programs stored in the storage unit 30. When the one or more processors execute the commands of the one or more programs stored in the storage unit 30, the processing unit 40 operates as one or more computers.

The processing unit 40 may include one or more dedicated hardware modules (such as an ASIC and an FPGA) configured to implement specific functions. In this case, the processing unit 40 may execute, as the one or more computers, processes described below that relate to assistance in creating the contents to be used in the interventions, or the dedicated hardware modules may execute at least some of these processes.

As shown, for example, in FIG. 2, as components that execute processes relating to the assistance in creating the contents to be used in the interventions, the processing unit 40 includes an intervention implementation unit 41, an estimation-model generation unit 42, a contribution-degree calculation unit 43, and a screen generation unit 44.

The intervention implementation unit 41 executes a process for implementing the interventions with respect to the targets to be intervention targets. If the advertising on the WEB site is implemented as the "interventions," for example, the intervention implementation unit 41 may execute a process as a DSP (Demand Side Platform) that wins a bid for advertising spaces on the WEB site in response to the request from the advertiser, and that distributes advertisements to the WEB site.

The estimation-model generation unit 42 executes a process of generating an estimation model for estimating predicted intervention effects from predetermined attributes of the targets. Among the predicted intervention effects, one predicted-intervention effect on a certain one of the targets is a numerical value corresponding to an increase in gain to the beneficiary (such as a purchase rate of an advertised commercial product or the like), the gain being expected to be larger in a case where the intervention is implemented to this certain one of the targets than in a case where the intervention is not implemented thereto.

For example, on the basis of target attribute information 311 (FIG. 5) about predetermined attributes (such as sexes and ages) of each of the plurality of targets, the estimation-model generation unit 42 generates the estimation model for the predicted intervention effects that represent predicted effects of the interventions if the interventions are implemented. Specifically, on the basis of intervened-group result information 341 (FIG. 4B), non-intervened-group result information 342 (FIG. 4C), and the target attribute information 311 (FIG. 5), the estimation-model generation unit 42 generates an estimation model for estimating the predicted intervention effects from the predetermined attributes of the targets (below, sometimes referred to as "target attributes").

The intervened-group result information 341 (FIG. 4B) contains information items about respective results of reactions by ones in an intervened group among the plurality of targets (such as whether or not he/she has purchased the advertised commercial product or the like), the ones having been subjected to the interventions, the intervened group consisting of these ones among the plurality of targets.

The non-intervened-group result information 342 (FIG. 4C) contains information items about respective results of reactions by other ones in a non-intervened group among the plurality of targets, the other ones having not been subjected to the interventions, the non-intervened group consisting of these other ones among the plurality of targets.

The target attribute information 311 (FIG. 5) contains information items about the respective attributes of the targets belonging to the intervened group or the non-intervened group.

A plurality of attribute items (such as sexes and ages) included as the predetermined attributes of the targets are respectively indicated by features. The estimation model to be generated by the estimation-model generation unit 42 is, for example, a model that allows numerical values to be estimated as the predicted intervention effects, the numerical values each corresponding to a sum of products obtained by multiplying the plurality of features corresponding to the plurality of attribute items respectively by weighting coefficients, that is, a linear model. Application of the respective target attributes of the targets to the estimation model, the attributes being included in the target attribute information 311 (FIG. 5), enables calculation of the respective predicted-intervention effects on the targets (FIG. 7).

The contribution-degree calculation unit 43 executes, on the basis of the estimation model obtained from the estimation-model generation unit 42, a process of calculating contribution degrees that indicate respective degrees by which the plurality of attribute items (such as sexes and ages) included as the predetermined attributes of the targets contribute to the predicted intervention effects. For example, when the estimation model is generated, the estimation model allowing the numerical values to be estimated as the predicted intervention effects, the numerical values each corresponding to the sum of the products obtained by multiplying the plurality of features corresponding to the plurality of attribute items respectively by the weighting coefficients, the contribution-degree calculation unit 43 calculates, among the contribution degrees, a corresponding-one contribution degree of one attribute item among the attribute items on the basis of, among the weighting coefficients, a corresponding-one weighting coefficient by which a corresponding one feature among the plurality of features is multiplied, the corresponding one feature corresponding to the one attribute item.

The screen generation unit 44 executes a process of generating display screens to be displayed on a display of the information processing apparatus 2 that accesses the server apparatus 1. The screen generation unit 44 generates the display screens so that, when the operations by the user (content creator) are input to the information processing apparatus 2, information is provided in accordance with these operations in a manner that the display screens are updated in response to these operations.

The screen generation unit 44 displays, on the display screen, at least some of the contribution degrees calculated respectively with regard to the plurality of attribute items included as the predetermined attributes of the targets. This enables the content creator to advance the work of creating the contents while checking what kind of the attribute items contributes to the predicted intervention effects. With this, contents having greater intervention effects are easily created.

FIG. 3A is a table showing an example of the target information 31 to be stored in the storage unit 30. In the target information 31 shown in FIG. 3A, target IDs for identifying the targets from each other and the target attributes are associated with each other. The attribute items such as sexes, ages, regions where the targets live, occupations, and the number of times of visits to a particular WEB site are included as the target attributes exemplified in FIG. 3A. The target information 31 may further contain, as the information items to be associated with the target IDs, information items other than the target attributes (for example, management information items such as dates when the information items are registered and expiration dates). The target attribute information 311 shown in FIG. 5 is an extract of ones of the target attributes from the target information 31, the ones being necessary for generating the estimation model for the predicted intervention effects.

FIG. 3B is a table showing an example of the intervention information 32 to be stored in the storage unit 30. In the intervention information 32 shown in FIG. 3B, intervention IDs for identifying implemented interventions from each other and predetermined attributes of the interventions (below, sometimes referred to as "intervention attributes") are associated with each other. Attribute items such as categories of commercial products to be advertised by interventions, content IDs indicating contents used in the interventions, and the numbers of times of repeating the interventions are included as the intervention attributes exemplified in FIG. 3B. The intervention information 32 may further contain, as the information items to be associated with the intervention IDs, information items other than the intervention attributes (for example, the management information items).

FIG. 3C is a table showing an example of the content information 33 to be stored in the storage unit 30. In the content information 33 shown in FIG. 3C, the content IDs for identifying the contents to be used in the interventions from each other and predetermined attributes of the contents (below, sometimes referred to as "content attributes") are associated with each other. Attribute items such as the numbers of characters to be contained in the contents, whether or not humans are depicted, whether or not animals are depicted, and background colors of the contents are included as the content attributes exemplified in FIG. 3C. The content information 33 may further contain, as the information items to be associated with the content IDs, information items other than the content attributes (for example, the management information items).

Figure 10:
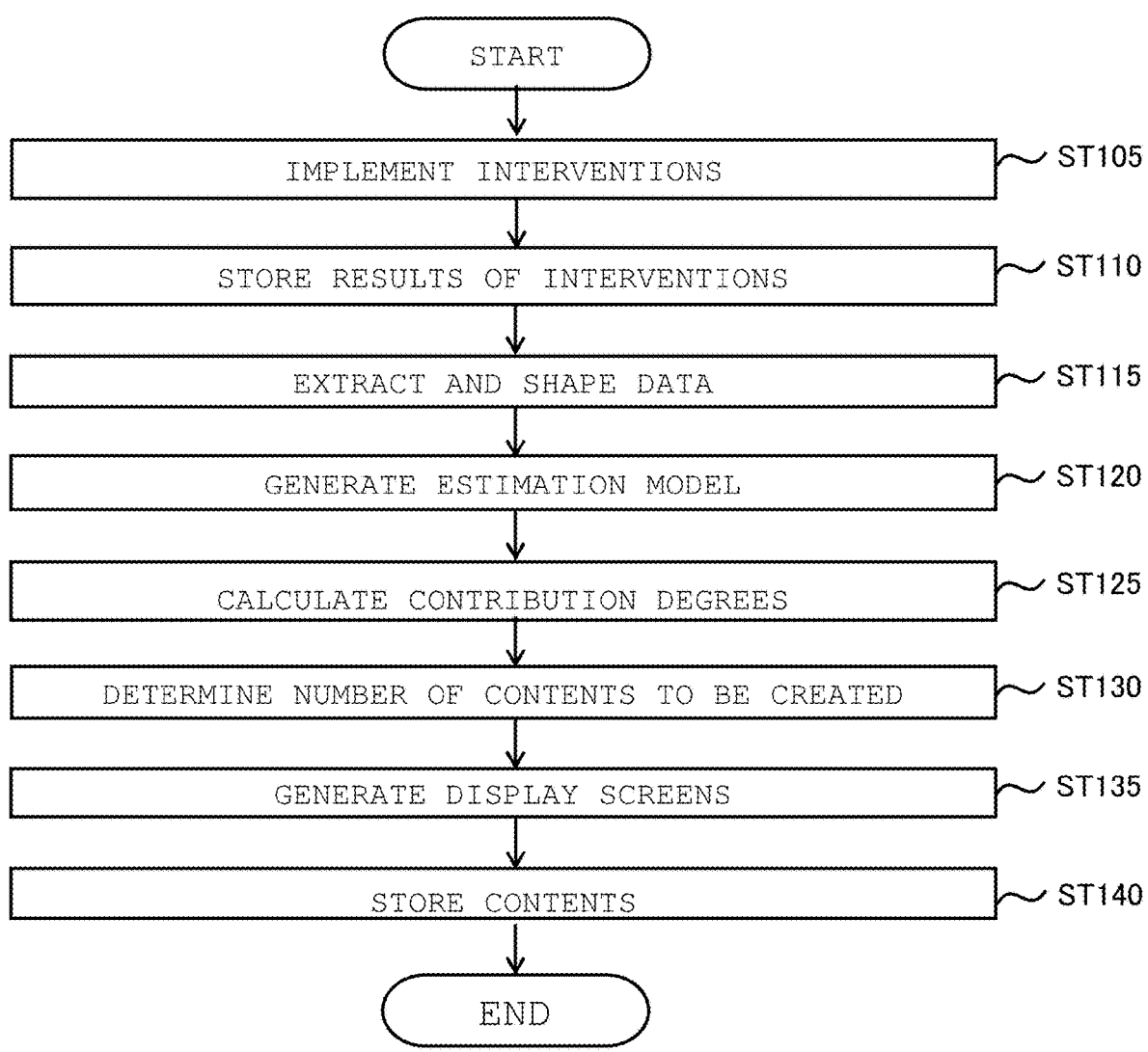
FIG. 10 is an explanatory flowchart showing an example of operations in the server apparatus according to the embodiment of the present invention.

Now, the operations in the server apparatus 1 according to this embodiment, the server apparatus 1 having the above-described configuration, are described with reference to a flowchart of FIG. 10.

ST105:

The intervention implementation unit 41 implements the interventions for obtaining the information (result information 34 shown in FIG. 4A) to be used at a time when the estimation model for the predicted intervention effects is generated in Step ST120 described below. The intervention implementation unit 41 implements the interventions with respect to a group of the ones of the targets, the ones being selected as targets in the intervened group, and meanwhile, does not implement the interventions with respect to another group of the other ones of the targets, the other ones being selected as targets in the non-intervened group. To which of the intervened group and the non-intervened group the targets belong may be selected at random, or may be selected according to some predetermined rules.

Note that, in a case where, for example, the advertisement distributions are implemented as the interventions, when the intervention (advertisement distribution) is repeatedly implemented to the same target, an effect of this intervention may decrease, or may even be negative. As a countermeasure, the number of the targets to be selected as those in the intervened group from the target information 31 may be set to the number that satisfies a predetermined proportion to all the selectable targets in the target information 31, or to the number that is fixed and is necessary and sufficient for generating the estimation model for the predicted intervention effects.

ST110:

The intervention implementation unit 41 records the result information 34 (FIG. 4A) to the storage unit 30, the result information 34 containing, respectively with regard to the targets belonging to the intervened group or the non-intervened group, whether or not the interventions have been implemented, contents of the implemented interventions, the results of the reactions by the targets, and the like. Note that, if the results of the reactions by the targets are results of whether or not he/she has purchased a commercial product, binary data (1 or 0) may be recorded as the results of the reactions. Alternatively, the results of the reactions by the targets may be continuous values such as purchase prices of commercial products.

ST115:

The estimation-model generation unit 42 extracts information items about the target attributes of the targets from the target information 31 (FIG. 3A), the information items being used in generating the estimation model for the predicted intervention effects. Then, the estimation-model generation unit 42 stores the extracted information items as the target attribute information 311 (FIG. 5) to the storage unit 30. In this example, the targets IDs in the target attribute information 311 (FIG. 5) are systematized in the same way as the target IDs in the result information 34 (FIG. 4A) are systematized. Note that, when it may be assumed that, among the targets, ones having target attributes similar to each other take similar actions in response to the interventions, the target IDs in the target attribute information 311 and the target IDs in the result information 34 may be systematized in different ways, that is, need not necessarily be directly linked to each other.

ST120:

By using the intervened-group result information 341 (FIG. 4B) and the non-intervened-group result information 342 (FIG. 4C) that are contained in the result information 34

(FIG. 4A) obtained by the interventions in Step ST100, and by using the target attribute information 311 extracted in Step ST115, the estimation-model generation unit 42 generates the estimation model to be used for estimating the respective predicted-intervention effects on the targets. The estimation-model generation unit 42 generates, by machine learning, estimation models for targets for whom information items in both the result information 34 obtained as a result of the interventions and the target attribute information 311 have been prepared, the estimation models being models for estimating the predicted intervention effects from the target attributes.

For example, the estimation-model generation unit 42 generates a first-gain estimation model $\mu_1$ for estimating gain to be obtained when the interventions are implemented (such as purchase rates of commercial products) from the target attributes on the basis of the intervened-group result information 341 (FIG. 4B) and of the target attribute information 311 (FIG. 5). In addition, the estimation-model generation unit 42 generates a second-gain estimation model $\mu_0$ for estimating gain to be obtained when the interventions are not implemented from the target attributes on the basis of the non-intervened-group result information 342 (FIG. 4C) and of the target attribute information 311 (FIG. 5). The first-gain estimation model $\mu_1$ and the second-gain estimation model $\mu_0$ can be generated by learning with use of existing algorithms of regression and classification (such as logistic regression).

FIG. 6A is a table showing the intervened-group result information 341 and the target attribute information 311 to be used in generating the first-gain estimation model $\mu_1$, and FIG. 6B is a table showing the non-intervened-group result information 342 and the target attribute information 311 to be used in generating the second-gain estimation model $\mu_0$. When the features indicating the target attributes are "X," and when the gain (such as the purchase rates of the commercial products) is "Y," the gain Y that is estimated by the first-gain estimation model $\mu_1$ is expressed by "$\mu_1(X)$," and the gain Y that is estimated by the second-gain estimation model $\mu_0$ is expressed by "$\mu_0(X)$."

Among the predicted intervention effects, a corresponding-one predicted intervention effect on one target among the targets can be calculated as a difference obtained by subtracting the gain estimated by applying, among the target attributes, a corresponding-one target attribute of the one target to the second-gain estimation model $\mu_0$ from the gain estimated by applying the corresponding-one target attribute of the one target to the first-gain estimation model $\mu_1$. For example, when, among the features, a feature indicating the corresponding-one target attribute of the one target is "$X_{new}$," the estimation-model generation unit 42 calculates a predicted intervention effect $\tau(X_{new})$ of the one target by the following equation.

[Math 1]

$$\tau(X_{new}) = \mu_1(X_{new}) - \mu_0(X_{new}) \quad (1)$$

When the gain is the purchase rate of the commercial product or the like, the predicted intervention effect $\tau(X_{new})$ expressed by Equation (1) corresponds to a result of subtraction of a predicted purchase rate ($\mu_0(X_{new})$) at the time when the intervention is not implemented from a predicted purchase rate ($\mu_1(X_{new})$) at the time when the intervention is implemented. FIG. 7 is a table showing an example of the predicted intervention effects calculated respectively with regard to the targets in the target information 31.

When both the first-gain estimation model $\mu_1$ and the second-gain estimation model $\mu_0$ are the linear models, an estimation model for the predicted intervention effects, the estimation model being expressed by Equation (1), is also the linear model. In other words, by the estimation model that is expressed by Equation (1), the numerical values each corresponding to the sum of the products obtained by multiplying the plurality of features corresponding to the plurality of attribute items respectively by the weighting coefficients are each estimated as the predicted intervention effect. FIG. 8 is a table showing an example of the respective weighting coefficients of the attribute items in the linear estimation model. In the example shown in FIG. 8, the sexes and the ages are used as discrete features, and the number of times of visits to a WEB site is used as a continuous-value feature. All the features are appropriately normalized such that, for example, an average is zero and a variance is one. Whether weights in this case are positive or negative corresponds to whether the intervention effects are positive or negative, and an increase in absolute value of the weights represents an increase in contribution degree to the intervention effects.

ST125:

The contribution-degree calculation unit 43 calculates, on the basis of the estimation model acquired in Step ST120, the contribution degrees that indicate the respective degrees by which the plurality of attribute items (such as sexes and ages) included as the predetermined attributes of the targets contribute to the predicted intervention effects. For example, when the linear estimation model as expressed by Equation (1) is acquired, the contribution-degree calculation unit 43 calculates, among the contribution degrees, a corresponding-one contribution degree of one attribute item among the attribute items on the basis of, among the weighting coefficients, a corresponding-one weighting coefficient by which a corresponding one feature among the plurality of features is multiplied, the corresponding one feature corresponding to the one attribute item. When the features are appropriately normalized, the contribution-degree calculation unit 43 may, for example, acquire the weighting coefficients respectively as the contribution degrees of the attribute items. Plus signs and minus signs of the weighting coefficients in this case correspond to plus signs and minus signs of the intervention effects, and an increase in absolute value of the weighting coefficient represents an increase in contribution degree to the intervention effects.

Alternatively, the contribution-degree calculation unit 43 may calculate the respective contribution degrees of the attribute items with use of a model that can be understood by humans, such as a decision tree, the model being generated by relearning with use of the predicted intervention effects to be obtained from the estimation model acquired in Step ST120. In other words, a technique for enabling description of the calculation of the contribution degrees with regard to the features without dependence on the original estimation model acquired in Step ST120 may be adopted.

For example, the contribution-degree calculation unit 43 calculates the respective predicted-intervention effects on the plurality of targets on the basis of the target attribute information 311 (FIG. 5) about the predetermined attributes of each of the plurality of targets, and on the basis of the estimation model acquired in Step ST120. The contribution-degree calculation unit 43 classifies the plurality of targets according to the plurality of attribute items with the predicted intervention effects being regarded as response variables, the classifying being performed with use of the model such as the decision tree (regression tree), the model being generated by learning on the basis of the predicted intervention effects calculated respectively with regard to the plurality of targets, and on the basis of the target attribute information 311 (FIG. 5). Then, the contribution-degree calculation unit 43 calculates the contribution degrees of the plurality of attribute items each on the basis of an average of the predicted-intervention effects on all the plurality of targets, each on the basis of a corresponding one of respective averages of the predicted-intervention effects on a group of targets classified according to the plurality of attribute items, and each on the basis of a corresponding one of the headcounts of the group of targets classified according to the plurality of attribute items.

Figure 9:
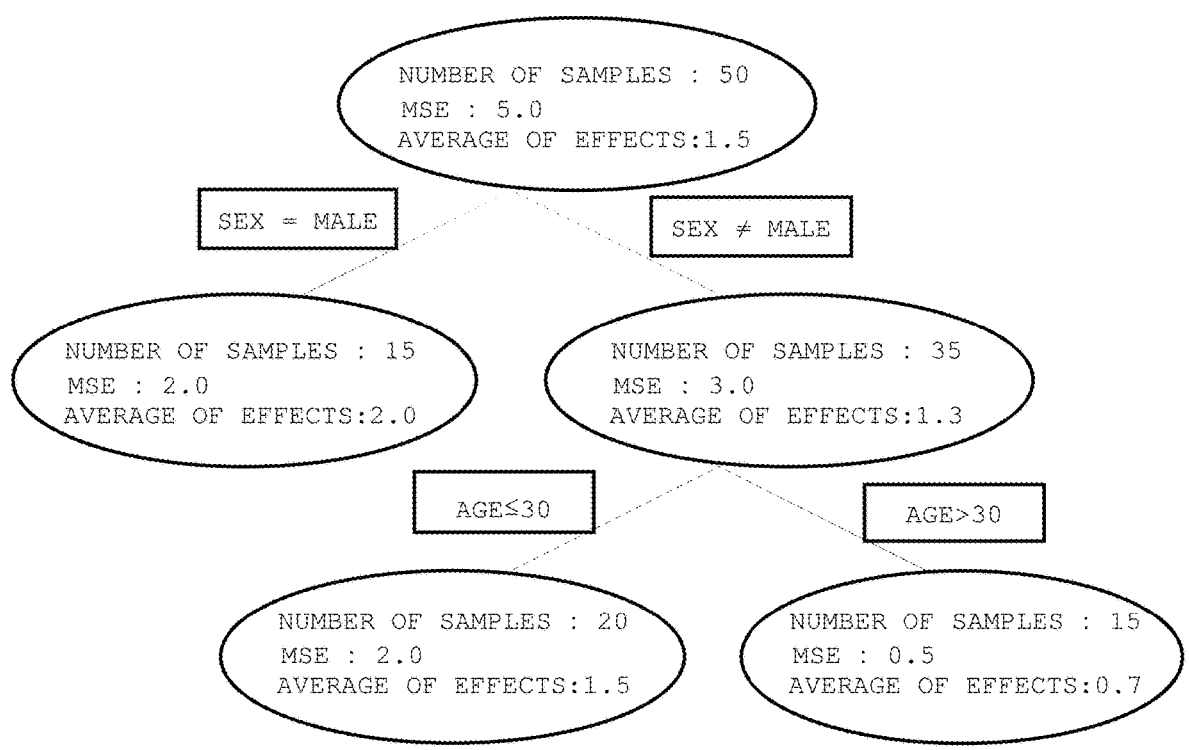
FIG. 9 is a chart showing an example of results obtained by analyzing a tendency of the predicted intervention effects corresponding to the attribute items of the targets with a decision tree.

FIG. 9 is a chart showing an example of results obtained by analyzing a tendency of the predicted intervention effects corresponding to the attribute items of the targets with use of the decision tree (regression tree). The response variables in learning for generating this estimation model are transformed outcomes. How much the features contribute to which of positives and negatives of the predicted intervention effects can be grasped, for example, by evaluating how much higher (or lower) each of the average values of the predicted intervention effects on ones of the targets, the ones corresponding to a certain one of the attribute items, are than the average value of the predicted intervention effects on all the targets, the evaluating being performed with regard to each of the attribute items that are split in the decision tree and being performed in consideration of the number of the ones of the targets. Thus, the respective contribution degrees of the attribute items can each be calculated, for example, as a product obtained by multiplying, by the number of the ones of the targets, the ones corresponding to a certain one of the attribute items, a difference between a corresponding one of the average values of the predicted intervention effects on the ones of the targets and the average value of the predicted intervention effects on all the targets.

In the example shown in FIG. 9, the respective contribution degrees of the attribute items, the degrees being classified with use of the decision tree, can be calculated as follows.

Sex—Male: 15×(2.0−1.5)=+7.5

Sex—Female (≠Male): 35×(1.3−1.5)=−7.0

Sex—Female at or over age of 30: 20×(1.5−1.5)=0

Sex—Female under age of 30: 15×(0.7−1.5)=−12.0

What whether the contribution degrees calculated in such a way are positive or negative and their absolute values represent is the same as what whether the weighting coefficients of the linear model described above are positive or negative and their absolute values represent.

ST130:

The processing unit 40 executes a process of determining the number of the contents to be created in accordance with reward that is set by the beneficiary. This reward is presented by the beneficiary for the work of creating the contents. The content creator creates the contents as many as the number of the contents to be created, the number having been determined in accordance with the reward.

Figure 11:
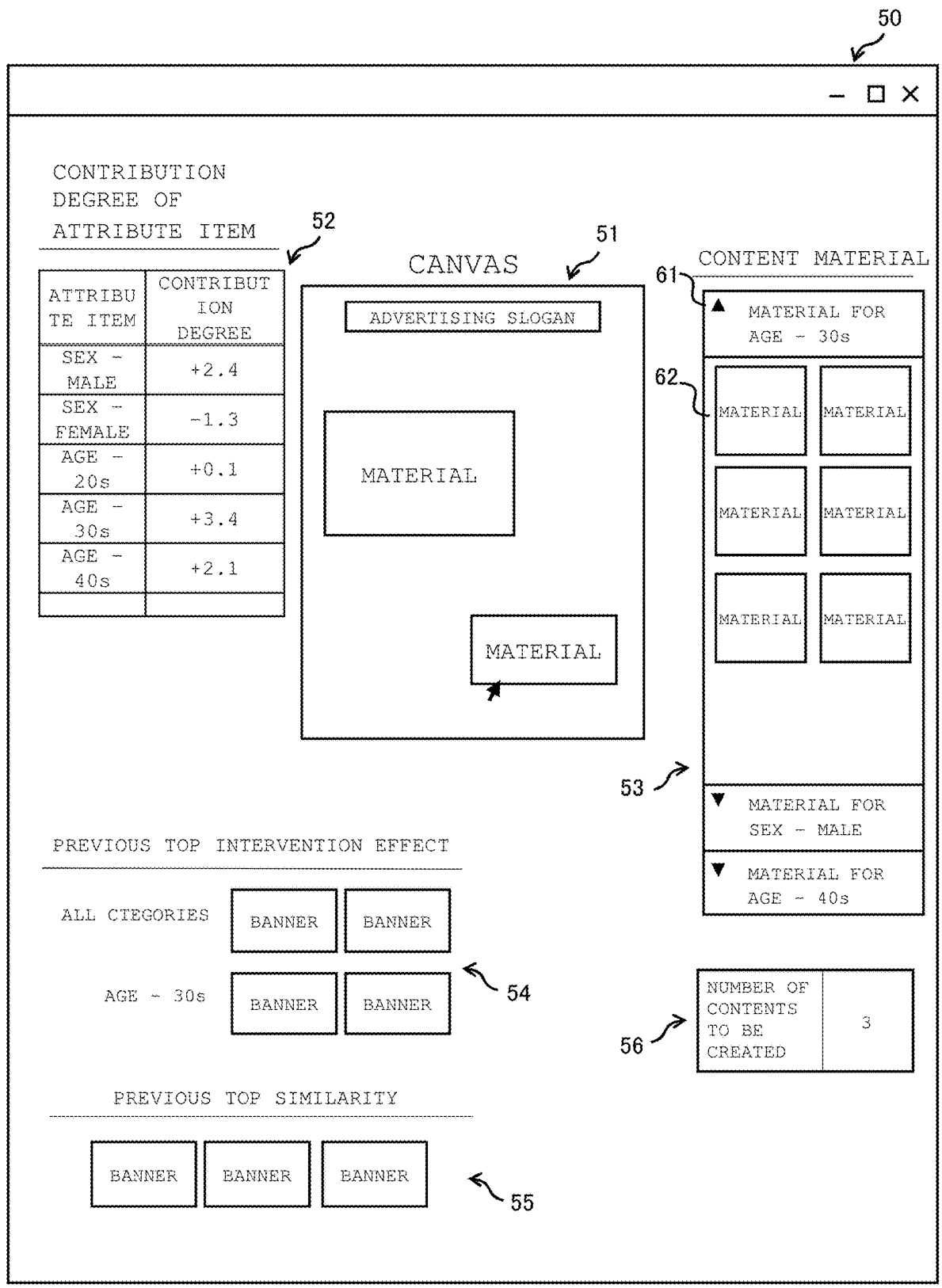
FIG. 11 is a view showing an example of a display screen for work of creating contents.

ST135:

The screen generation unit 44 executes the process of generating the display screens that can be displayed on the display of the information processing apparatus 2 to be used in the work of creating the contents. FIG. 11 is a view showing an example of a display screen 50 to be generated by the screen generation unit 44. In a central portion of the display screen 50 shown in FIG. 11, a window 51 that defines an area in which the contents such as banners are created is provided. In the window 51, content materials (such as photographs, illustrations, graphics, and a window in which characters of an advertising slogan are displayed) are arranged. The user (content creator) arbitrarily selects the content materials by operating icons with a mouse or the like. With this, the content materials can be arranged at arbitrary positions in the window 51.

The screen generation unit 44 displays, on the display screen, at least some of the contribution degrees calculated respectively with regard to the plurality of attribute items. For example, in an upper left area of the display screen 50 shown in FIG. 11, a list 52 that is entitled "CONTRIBUTION DEGREE OF ATTRIBUTE ITEM" and shows respective contribution degrees of the attribute items is displayed. With this, the user (content creator) can easily create contents having greater intervention effects while checking the contribution degrees corresponding to the attribute items.

In addition, the content materials (materials of the contents) to be displayed on the display screen by the screen generation unit 44 may be displayed in a manner of corresponding to the contribution degrees of the attribute items (such as sexes and ages). For example, the storage unit 30 stores content materials (such as a photograph of a person for women and an advertising slogan for young people) associated with the attribute items (such as sexes and ages) of the targets. The screen generation unit 44 selects one or more content materials among the plurality of content materials each associated with at least one attribute item among the plurality of attribute items, the one or more content materials being associated with, among the plurality of attribute items, attribute items having relatively-high contribution degrees among the contribution degrees. The screen generation unit 44 displays, on the display screen, the selected one or more content materials as a candidate for the content materials that can be used in creating the contents.

For example, near an end portion on the right of the display screen 50 shown in FIG. 11, a content-material arrangement field 53 for enabling the user to arbitrarily select the content materials is provided. The content-material arrangement field 53 includes a plurality of fields 62 that can be collapsed by operations to their respective tabs 61. The plurality of content materials associated with a common one of the attribute items are arranged in each of the fields 62. In a state exemplified in FIG. 11, among the fields 62, a field 62 in which content materials that are for 30s having highest contribution degrees are arranged is developed. With this, content materials associated with attribute items having relatively-high contribution degrees are easily used in creating the contents.

In addition, in the content-material arrangement field 53 on the display screen 50 shown in FIG. 11, the plurality of fields 62 are arranged in a manner that, as contribution degrees of attribute items to which ones of the content materials correspond become higher, among the fields 62, fields 62 including these ones of the content materials are located higher. In other words, in displaying the plurality of content materials associated with the attribute items having relatively-high contribution degrees on the display screen 50, the screen generation unit 44 arranges the plurality of content materials in an order corresponding to the contribution degrees of the attribute items with which the content materials are associated. With this, contribution degrees can be easily grasped from the order of the arrangement of the content materials.

Further, the screen generation unit 44 may display, on the display screen 50, contents used in interventions that have caused relatively-great intervention effects in previous interventions (for example, immediately preceding interventions). For example, the screen generation unit 44 selects one or more contents among a plurality of contents that are used in the previous interventions, the one or more contents corresponding to relatively-high averages among averages of the predicted interventions effects on all targets to which the interventions have been implemented, and displays the selected one or more contents as reference information on the display screen 50.

For example, near a center on the left of the display screen 50 shown in FIG. 11, a field 54 in which the contents (such as banners) that are used in the previous interventions are arranged is provided. In this field 54, upper two of the contents indicate two contents that correspond to the relatively-high averages among the averages of the predicted interventions effects. With this, contents can be created with reference to contents that have caused great intervention effects among contents used in previous interventions. Thus, contents having greater intervention effects are easily created.

Still further, the screen generation unit 44 may display, on the display screen 50, contents that have caused relatively-great intervention effects on users with attributes having high contribution degrees among the contents used in the previous interventions. For example, the screen generation unit 44 acquires, with regard to the plurality of contents used in the previous interventions, respective relatively-high averages among the averages of the predicted intervention effects on some targets among all targets to which the interventions have been implemented (some targets corresponding to one or more attribute items among the plurality of attribute items, the one or more attribute items having relatively-high contribution degrees). The screen generation unit 44 selects, from the plurality of contents used in the previous interventions, one or more contents corresponding to these relatively-high averages among the averages of the predicted intervention effects. The screen generation unit 44 displays this selected one or more contents as the reference information on the display screen 50.

For example, in the field 54 on the display screen 50 shown in FIG. 11, lower two of the contents (banners) indicate two contents used in interventions that correspond to relatively-high averages among averages of the predicted intervention effects on targets in their "30s" who have the highest contribution degrees. With this, contents can be created with reference to contents that have caused great intervention effects on targets with attributes having high contribution degrees among contents used in previous interventions. Thus, contents having great effects exclusively on the targets with the attributes having high contribution degrees are easily created.

Yet further, the screen generation unit 44 may calculate respective similarities between a plurality of previously created contents and currently created contents on the display screen 50, select, from the plurality of created contents, one or more created contents having relatively high similarities among the respective similarities, and display the selected one or more created contents as the reference information on the display screen 50. The similarities between the contents may be calculated, for example, from similarities between images of the contents, similarities between combinations of content materials used in the contents, or from overlapping degrees of character strings in the contents.

For example, on a lower left side of the display screen 50 shown in FIG. 11, a field 55 in which three contents (banners) that have relatively-high similarities to the currently created contents is provided. By referring to the previously created contents that are similar to the currently created contents in this way, an efficiency in creating contents is easily increased. In addition, commonalities to and differences from the previously created contents can be checked, and hence various and diverse contents are easily created.

Yet further, the screen generation unit 44 may display, on the display screen 50, information about the number of the contents to be created, the number being determined in Step ST130. On the display screen 50 shown in FIG. 11, a field 56 in which the number of the contents to be created is displayed is provided at a lower right corner. With this, work can be efficiently advanced while the number of the contents to be created is checked.

ST140:

The processing unit 40 stores the contents created on the display screen 50 generated by the screen generation unit 44 as the created contents into the storage unit 30. For example, the processing unit 40 registers the information items about the contents as shown in FIG. 3C with the content information 33.

As described hereinabove, according to this embodiment, the contribution degrees that indicate respective degrees by which the plurality of attribute items included as the predetermined attributes of the targets contribute to the predicted intervention effects are calculated on the basis of the estimation model for estimating the predicted intervention effects from the predetermined attributes. Then, at least some of the contribution degrees calculated respectively with regard to the plurality of attribute items are displayed on the display screen for work of creating contents. With this, the work of creating contents can be advanced while what kind of the attribute items contributes to the predicted intervention effects is checked. Thus, contents having greater intervention effects are easily created.

Note that, the present invention is not limited only to the above-described embodiment, and may be embodied in various other forms that persons skilled in the art could easily conceive.

The display screen 50 for work of creating contents, the screen being shown in FIG. 11, is merely an example, and the present invention is not limited to this example. Specifically, the arrangement and visual forms such as sizes of the fields on the display screen 50 are merely examples, and may be arbitrarily changed. In addition, the contents to be created while being assisted are not limited to the banners for advertising, and may be, for example, contents including moving images and voice.

The invention claimed is:

1. An apparatus configured to assist in creation of contents to be used in interventions, the apparatus comprising:
   a processing unit including at least one processor; and
   a storage unit configured to store a command to be executed by the processing unit,
   wherein the interventions include presentation of the contents to a plurality of targets so that the plurality of targets provoke reactions that a beneficiary wants,
   wherein, among respective predicted-intervention effects on the plurality of targets, one predicted-intervention effect on one target among the plurality of targets is a numerical value corresponding to an increase in gain to the beneficiary, the gain being larger in a case where a corresponding single intervention among the interventions is implemented to the one target than in a case where the corresponding single intervention is unimplemented to the one target, wherein the gain is a numerical value that is set in accordance with a result of a corresponding one reaction by the one target among the reactions, wherein the processing unit executes, in accordance with the command, a process of calculating contribution degrees that indicate respective degrees by which a plurality of attribute items included as predetermined attributes of the one target contribute to the one predicted-intervention effect, the calculating being performed on a basis of an estimation model for estimating the one predicted-intervention effect from the predetermined attributes of the one target, and a process of generating a display screen that can be displayed on a display to be used in work of creating the contents, wherein the process of generating the display screen includes generating the display screen on which at least one contribution degree among the contribution degrees calculated respectively with regard to the plurality of attribute items is displayed, wherein the plurality of attribute items is respectively indicated by a plurality of features, wherein the estimation model is a model that estimates a numerical value as the one predicted-intervention effect, the numerical value corresponding to a sum of products obtained by multiplying the plurality of features corresponding to the plurality of attribute items respectively by weighting coefficients, and wherein the process of calculating the contribution degrees includes calculating, among the contribution degrees, a corresponding-one contribution degree of one attribute item among the plurality of attribute items on a basis of, among the weighting coefficients, a corresponding-one weighting coefficient by which a corresponding one feature among the plurality of features is multiplied, the corresponding one feature corresponding to the one attribute item.

2. The apparatus according to claim 1, wherein the process of calculating the contribution degrees includes calculating the respective predicted-intervention effects on the plurality of targets
     on a basis of target attribute information about the predetermined attributes of each of the plurality of targets, and
     on the basis of the estimation model, classifying the plurality of targets according to the plurality of attribute items with the respective predicted-intervention effects being regarded as response variables, the classifying being performed
     on a basis of the respective predicted-intervention effects calculated with regard to the plurality of targets, and
     on the basis of the target attribute information, and calculating the contribution degrees of the plurality of attribute items,
     each on a basis of an average of the respective predicted-intervention effects on all the plurality of targets,
     each on a basis of a corresponding one of respective averages of the respective predicted-intervention effects on a group of targets classified according to the plurality of attribute items, and
     each on a basis of a corresponding one of the headcounts of the group of targets classified according to the plurality of attribute items.

3. The apparatus according to claim 1, wherein the contents are made of a plurality of content materials each associated with at least one attribute item among the plurality of attribute items, and wherein the process of generating the display screen includes selecting at least one content material among the plurality of content materials, the at least one content material being associated with, among the plurality of attribute items, one attribute item having a relatively-high contribution degree among the contribution degrees, and generating the display screen on which the selected at least one content material is displayed as a candidate for the plurality of content materials that can be used in creating the contents.

4. The apparatus according to claim 3, wherein the process of generating the display screen includes selecting the plurality of content materials, and generating the display screen on which the selected plurality of content materials is arranged in an order corresponding to the contribution degrees of the plurality of attribute items with which the plurality of content materials are associated.

5. The apparatus according to claim 1, wherein the intervention includes previous interventions, wherein the contents include a plurality of contents used in the previous interventions, wherein the respective predicted-intervention effects on the plurality of targets include other respective predicted-intervention effects on all the plurality of targets to which the interventions have been implemented, and a still other predicted-intervention effect on at least one target among all the plurality of targets to which the interventions have been implemented, the at least one target corresponding to at least one attribute item among the plurality of attribute items, the at least one attribute item having a high contribution degree among the contribution degrees, wherein the process of generating the display screen includes at least one of selecting, from the plurality of contents used in the previous interventions, at least one content corresponding to a high average among averages of the other respective predicted-intervention effects, or selecting, from the plurality of contents used in the previous interventions, at least one content corresponding to a high average among averages of the still other predicted-intervention effect, and wherein the process of generating the display screen includes generating the display screen on which the selected at least one content is displayed as reference information.

6. The apparatus according to claim 1, wherein the contents include a plurality of previously created contents, and wherein the process of generating the display screen includes calculating similarities between the plurality of previously created contents and currently created contents on the display screen, selecting, from the plurality of previously created contents, at least one previously-created content having a relatively high similarity among the similarities, and generating the display screen on which the selected at least one previously-created content is displayed as reference information.

7. The apparatus according to claim 1, wherein the processing unit executes a process of determining the number of the contents to be created, the process being executed in accordance with the command, the number being determined in accordance with reward that is set by the beneficiary, and wherein the process of generating the display screen includes generating the display screen on which information about the determined number of the contents to be created is displayed.

8. A method of assisting creation of contents to be used in interventions, the interventions including presentation of the contents to a plurality of targets so that the plurality of targets provoke reactions that a beneficiary wants, among respective predicted-intervention effects on the plurality of targets, one predicted-intervention effect on one target among the plurality of targets being a numerical value corresponding to an increase in gain to the beneficiary, the gain being expected to be larger in a case where a corresponding single intervention among the interventions is implemented to the one target than in a case where the corresponding single intervention is unimplemented to the one target, the gain being a numerical value that is set in accordance with a result of a corresponding one reaction by the one target among the reactions, the method comprising:

calculating, by at least one computer, contribution degrees that indicate respective degrees by which a plurality of attribute items included as predetermined attributes of the one target contribute to the one predicted-intervention effect, the calculating being performed on a basis of an estimation model for estimating the one predicted-intervention effect from the predetermined attributes of the one target; and generating, by the at least one computer, a display screen that can be displayed on a display to be used in work of creating the contents, wherein the generating of the display screen by the at least one computer includes generating the display screen on which at least one contribution degree among the contribution degrees calculated respectively with regard to the plurality of attribute items is displayed, wherein the plurality of attribute items is respectively indicated by a plurality of features, wherein the estimation model is a model that estimates a numerical value as the one predicted-intervention effect, the numerical value corresponding to a sum of products obtained by multiplying the plurality of features corresponding to the plurality of attribute items respectively by weighting coefficients, and wherein the process of calculating the contribution degrees includes calculating, among the contribution degrees, a corresponding-one contribution degree of one attribute item among the plurality of attribute items on a basis of, among weighting coefficients, a corresponding-one weighting coefficient by which a corresponding one feature among the plurality of features is multiplied, the corresponding one feature corresponding to the one attribute item.

9. A non-transitory computer-readable recording medium that records a program which assists creation of contents to be used in interventions, the interventions including presentation of the contents to a plurality of targets so that the plurality of targets provoke reactions that a beneficiary wants, among respective predicted-intervention effects on the plurality of targets, one predicted-intervention effect on one target among the plurality of targets being a numerical value corresponding to an increase in gain to the beneficiary, the gain being expected to be larger in a case where a corresponding single intervention among the interventions is implemented to the one target than in a case where the corresponding single intervention is unimplemented to the one target, the gain being a numerical value that is set in accordance with a result of a corresponding one reaction by the one target among the reactions, the program causing at least one computer to execute:

a process of calculating contribution degrees that indicate respective degrees by which a plurality of attribute items included as predetermined attributes of the one target contribute to the one predicted-intervention effect, the calculating being performed on a basis of an estimation model for estimating the one predicted-intervention effect from the predetermined attributes of the one target; and a process of generating a display screen that can be displayed on a display to be used in work of creating the contents, wherein the process of generating the display screen includes generating the display screen on which at least one contribution degree among the contribution degrees calculated respectively with regard to the plurality of attribute items is displayed, wherein the plurality of attribute items is respectively indicated by a plurality of features, wherein the estimation model is a model that estimates a numerical value as the one predicted-intervention effect, the numerical value corresponding to a sum of products obtained by multiplying the plurality of features corresponding to the plurality of attribute items respectively by weighting coefficients, and where the process of calculating the contribution degrees includes calculating, among the contribution degrees, a corresponding-one contribution degree of one attribute item among the plurality of attribute items on a basis of, among the weighting coefficients, a corresponding-one weighting coefficient by which corresponding one feature among the plurality of features is multiplied, the corresponding one feature corresponding to the one attribute item.

* * * * *